(12) United States Patent
Jhong et al.

(10) Patent No.: US 12,714,359 B2
(45) Date of Patent: Aug. 25, 2026

(54) METHOD AND SYSTEM FOR ANALYZING HAIR CHARACTERISTICS

(71) Applicant: MacroHI Co., Ltd., New Taipei City (TW)

(72) Inventors: Sin-Ye Jhong, New Taipei City (TW); Chih-Hsien Hsia, Taipei City (TW); Chun-Wei Chen, New Taipei City (TW)

(73) Assignee: MacroHI Co., Ltd., New Taipei City (TW)

( * ) Notice: Subject to any disclaimer, the term of this patent is extended or adjusted under 35 U.S.C. 154(b) by 274 days.

(21) Appl. No.: 18/367,441

(22) Filed: Sep. 12, 2023

(65) Prior Publication Data

US 2024/0404094 A1 Dec. 5, 2024

(30) Foreign Application Priority Data

May 29, 2023 (CN) ......................... 202310614302.7

(51) Int. Cl.
*A61B 5/00* (2006.01)
*G06N 3/045* (2023.01)
*G06T 7/00* (2017.01)

(52) U.S. Cl.
CPC .............. *A61B 5/448* (2013.01); *A61B 5/446* (2013.01); *G06N 3/045* (2023.01); *G06T 7/0012* (2013.01)

(58) Field of Classification Search
CPC ........ A61B 5/448; A61B 5/446; G06N 3/045; G06T 7/0012
See application file for complete search history.

(56) References Cited

U.S. PATENT DOCUMENTS

2021/0366614 A1* 11/2021 Chee Chong ........ A61B 5/7475
2023/0101556 A1 3/2023 Akerele et al.
2025/0259461 A1* 8/2025 Huang ................. G06V 20/695

FOREIGN PATENT DOCUMENTS

CN 109002798 A 12/2018
CN 112084965 A 12/2020
CN 112687392 A 4/2021
CN 215534281 U 1/2022
CN 114344188 A 4/2022
(Continued)

OTHER PUBLICATIONS

Lee et al., "An intelligent hair and scalp analysis system using camera sensors and Norwood-Hamilton model", Int J Innov Comput Inform Control, vol. 14, No. 2, Apr. 2018, pp. 503-518.
(Continued)

*Primary Examiner* — Casey L Kretzer
(74) *Attorney, Agent, or Firm* — Bruce Stone LLP; Joseph A. Bruce

(57) ABSTRACT

A hair feature analysis method and system are provided. The hair feature analysis method includes the steps of capturing high magnification and low magnification images of a scalp area and performing preprocessing on these images. The preprocessed high magnification and low magnification images are then input into an artificial intelligence model to simultaneously detect hair follicles and calculate hair widths in the scalp area. Hair characteristics are then calculated based on the analyzed high magnification and low magnification images. The artificial intelligence model can be an R-CNN model or a variant thereof.

10 Claims, 12 Drawing Sheets

(56) References Cited

FOREIGN PATENT DOCUMENTS

| | | | |
|---|---|---|---|
| TW | 201701821 | A | 1/2017 |
| TW | 202008951 | A | 3/2020 |
| WO | WO2021215749 | A1 | 10/2021 |

OTHER PUBLICATIONS

Bernardis et al., "Quantifying alopecia areata via texture analysis to automate the SALT score computation", J Investig Dermatol Symp Proc, 2018;19(1):S34-S40, vol. 19.
Kapoor et al., "Automated classification method for early diagnosis of alopecia using machine learning", Elsevier, Proc Comput Sci. 2018;132;437-443.
Kolasinski, "TrichoScan®: a useful method for measuring hair growth parameters and enhancing patient selection for hair restoration surgery", Hair Transplant Forum Int. 2009;19(2):56-59.
Kuklyte Jogile et al: "Evaluation of the Use of Single- and Multi-Magnification Convolutional Neural Networks for the Determination and Quantitation of Lesions in Nonclinical Pathology Studies", Toxicologic Pathology., [Online] vol. 49, No. 4, Feb. 23, 2021 (Feb. 23, 2021), pp. 815-842, XP093128676.
Chen Kai et al: "Hybrid Task Cascade Instance Segmentation", 2019 IEEE/CVF Conference on Computer Vision and Pattern Recognition (CVPR) , IEEE, Jun. 15, 2019 (Jun. 15, 2019), pp. 4969-4978, XP033687254.
Chang Wan-Jung et al: "ScalpEye: A Deep Learning-Based Scalp Hair Inspection and Diagnosis System for Scalp Health", IEEE Access, IEEE, USA, vol. 8, Jul. 21, 2020 (Jul. 21, 2020), 134826-134837, XP11801267A.
Rinmoy Roy et al: "Hair and Scalp Disease Detection using Machine Learning and Image Processing", arxiv.org, Cornell University Library, 201 Olin Library Cornell University Ithaca, NY 14853, Dec. 31, 2022 (Dec. 31, 2022), XP91522370A.

* cited by examiner

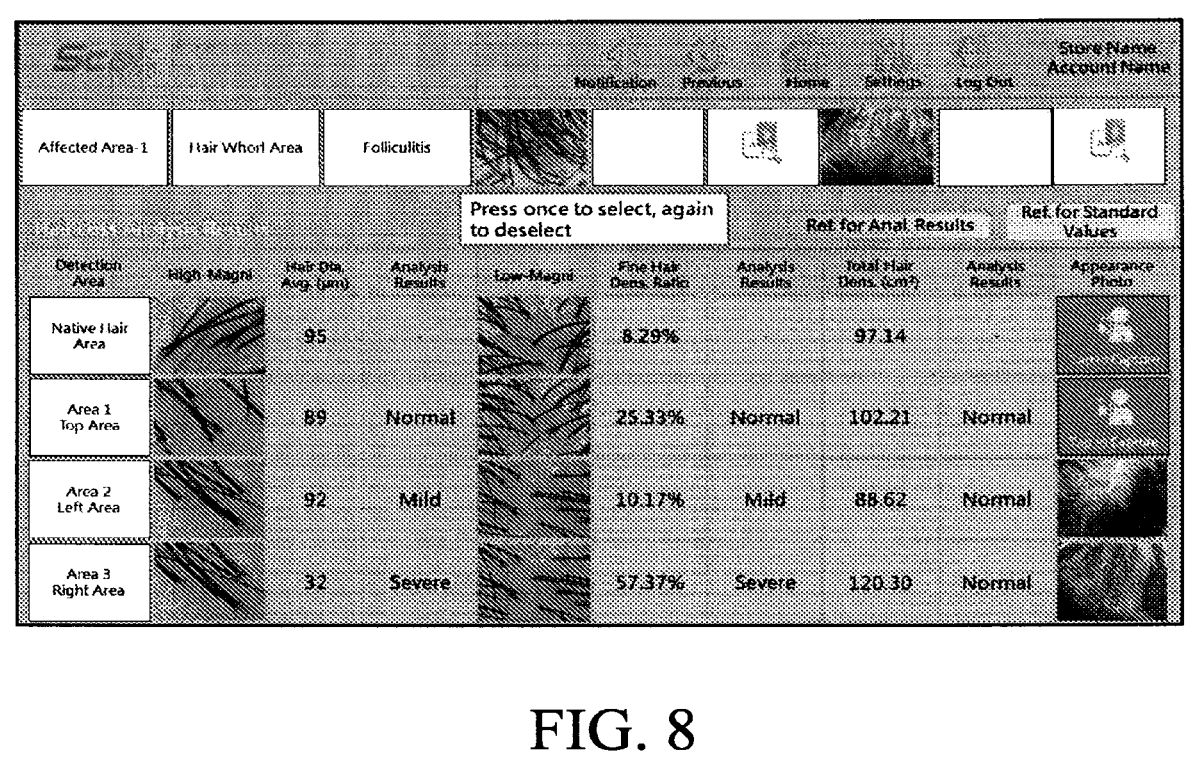

| Detection Area | High Magni | Hair Dia. Avg. (μm) | Analysis Results | Low Magni | Fine Hair Dens. Ratio | Analysis Results | Total Hair Dens. (cm²) | Analysis Results | Appearance Photo |
|---|---|---|---|---|---|---|---|---|---|
| Native Hair Area | | 95 | | | 8.29% | | 97.14 | - | |
| Area 1 Top Area | | 89 | Normal | | 25.33% | Normal | 102.21 | Normal | |
| Area 2 Left Area | | 92 | Mild | | 10.17% | Mild | 88.62 | Normal | |
| Area 3 Right Area | | 32 | Severe | | 57.37% | Severe | 120.30 | Normal | |

FIG. 8

METHOD AND SYSTEM FOR ANALYZING HAIR CHARACTERISTICS

BACKGROUND OF THE INVENTION

1. Field of the Invention

The present invention relates to a hair analysis system and method, particularly to a hair analysis system and method that uses an artificial intelligence model to analyze hair features, such as hair diameter, thin hair density ratio, and total hair density ratio.

2. Description of the Prior Art

Hair loss is a common problem affecting millions of people worldwide. Analyzing hair features, such as hair diameter, thin hair density ratio, and total hair density ratio, is crucial for diagnosing hair loss, assessing its severity, and determining appropriate treatment plans. Traditional hair analysis methods rely on manual inspection, which can be time-consuming, labor-intensive, and prone to human error. Moreover, these methods may lack accuracy and repeatability, as results may vary depending on the examiner's experience and skills. Recently, advancements in computer vision and artificial intelligence have made the development of automated hair analysis systems possible. These technologies typically use machine learning algorithms to process and analyze images of the scalp area, detect hair follicles, and calculate hair widths.

Therefore, how to utilize artificial intelligence models to meet the specific requirements of hair analysis tasks, to provide more accurate and consistent results in detecting hair follicles and calculating hair widths, ultimately contributing to more effective diagnosis and treatment of hair loss problems, is worth considering for persons who are skilled in the art.

SUMMARY OF THE INVENTION

The object of the present invention is to provide a method and system for analyzing hair features using an artificial intelligence model to meet the specific requirements of hair analysis tasks, providing more accurate and consistent results in detecting hair follicles and calculating hair widths.

Based on the above and other objects, the present invention provides a hair feature analysis method, which includes the following steps: first, high magnification and low magnification images of a scalp area are captured, and then these images are preprocessed. Next, the preprocessed high magnification and low magnification images are input into an artificial intelligence model to simultaneously detect hair follicles in the scalp area and calculate hair widths. Afterwards, at least one hair feature can be calculated from the high magnification and low magnification images analyzed by the artificial intelligence model. The artificial intelligence model can adopt an R-CNN model or a variant of the R-CNN model.

Based on the above and other objects, the present invention also provides a hair feature analysis system, which includes: an image capturing device, a preprocessing module, an artificial intelligence model, and an analysis module. The image capturing device is used to capture a high magnification and a low magnification image of a scalp area, and the preprocessing module is used to preprocess these images. The artificial intelligence model can simultaneously detect hair follicles and calculate hair widths, and the model can be an R-CNN model or a variant of the R-CNN model. In addition, the analysis module is used to receive the images analyzed by the artificial intelligence model and calculate at least one hair feature.

In the above-mentioned hair feature analysis method or system, the artificial intelligence model is an HTC enhanced model, which is modified from a hybrid task cascade model and has the following features: the model replaces the semantic segmentation module in the hybrid task cascade model with a global feature enhancement module and connects the refined semantic features from the global feature enhancement module with multiple framework branches. In addition, the model also introduces a framework-mask enhancement module, which is connected with the aforementioned framework branches and at least one mask branch.

In the above-mentioned hair feature analysis method or system, the HTC enhanced model has multiple features. Among them, the global feature enhancement module includes multiple convolutional layers with different kernel sizes to extract multi-scale features. In one embodiment, the HTC enhanced model has the framework branch and the mask branch at each stage, and there are multiple framework-mask enhancement modules, each of which is connected between the framework branch and the mask branch at each stage. In addition, in another embodiment, the HTC enhanced model has a framework branch at each stage but only one mask branch, and the framework-mask enhancement module is connected between the last framework branch and the mask branch.

In summary, by introducing the R-CNN model or its variants, the hair analysis method and system of the present invention can more accurately and consistently detect hair follicles and calculate hair widths, which helps to analyze and address hair loss problems more effectively.

The accompanying drawings are incorporated in and constitute a part of this application and, together with the description, serve to explain the principles of the invention in general terms. Like numerals refer to like parts throughout the disclosure.

BRIEF DESCRIPTION OF THE DRAWINGS

The objects, spirits, and advantages of the preferred embodiments of the present invention will be readily understood by the accompanying drawings and detailed descriptions, wherein:

FIG. 8 illustrates a visualization of the hair analysis results.

DETAILED DESCRIPTION OF THE INVENTION

In order to describe in detail the technical content, structural features, achieved objectives and effects of the instant application, the following detailed descriptions are given in conjunction with the drawings and specific embodiments. It should be understood that these embodiments are only used to illustrate the application and not to limit the scope of the instant application.

Figure 1A:
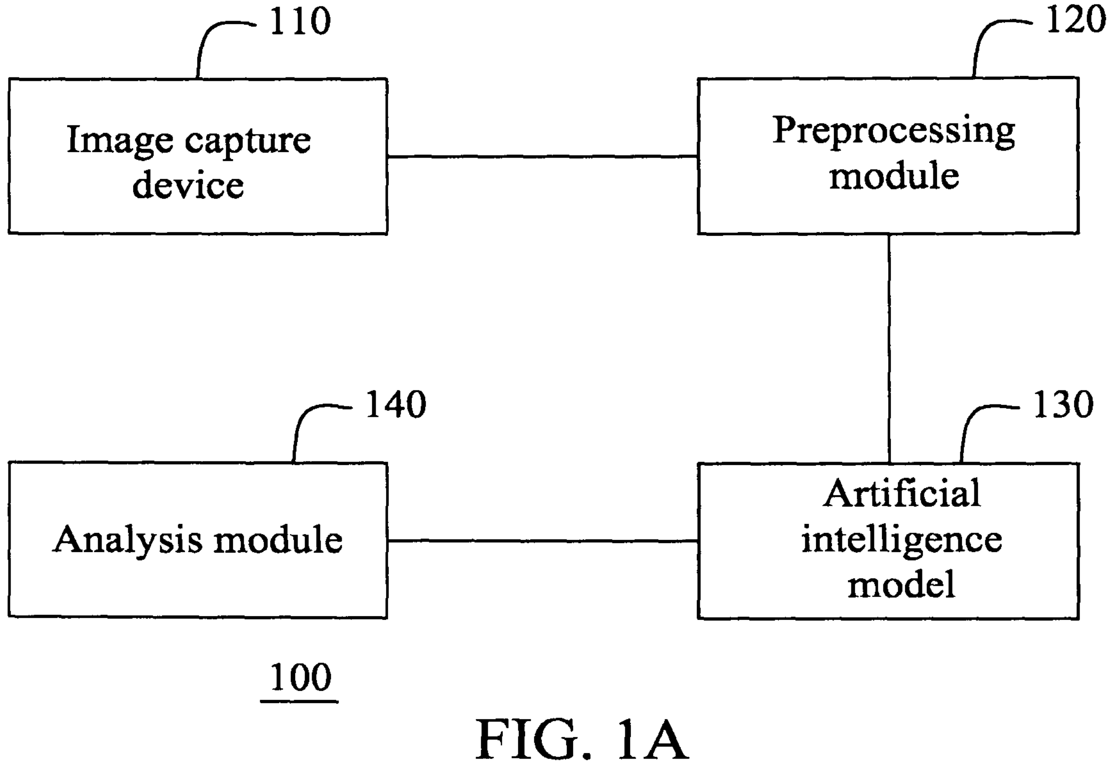
FIG. 1A shows a first embodiment of a hair feature analysis system of the present invention.

Please refer to FIG. 1A, which shows a first embodiment of a hair feature analysis system of the present invention. This hair feature analysis system 100 includes an image capture device 110, a preprocessing module 120, an artificial intelligence model 130, and an analysis module 140. The image capture device 110 is responsible for capturing high-magnification and low-magnification images of the scalp area. In this embodiment, the image capture device 110 can simultaneously capture high-magnification and low-magnification images of a scalp area. By simultaneously capturing high-magnification and low-magnification images, complementary information from two different images can be obtained, which helps to improve the accuracy and reliability of hair width and density measurements. These images provide detailed information about hair follicles and hair width, which is crucial for analyzing hair features. The preprocessing module 120 is responsible for preprocessing the captured high-magnification and low-magnification images, including noise reduction, resizing, normalization or other image enhancement techniques. In addition, the preprocessing module 120 can also evaluate the quality of the images. If the image quality is determined to be poor, it can command the image capture device 110 to recapture the image or notify the operator of the hair feature analysis system 100 to recapture the image.

The artificial intelligence model 130 is responsible for simultaneously detecting hair follicles from the preprocessed high-magnification and low-magnification images and calculating hair width. This artificial intelligence model 130 can be an R-CNN model or other variants of the R-CNN model, and more detailed introduction about what are the variants of the R-CNN model will be provided later. In addition, the analysis module 140 is responsible for analyzing the image and calculating hair features based on the output of the artificial intelligence model 130. Using the information provided by the artificial intelligence model 130, the analysis module 140 can perform further analysis, calculate the hair features of the scalp area, and provide personalized suggestions for hair care to understand the health of the hair and discover potential problems related to hair. The collaboration between this artificial intelligence model 130 and the analysis module 140 ensures a comprehensive and accurate assessment of hair health and characteristics.

Figure 1B:
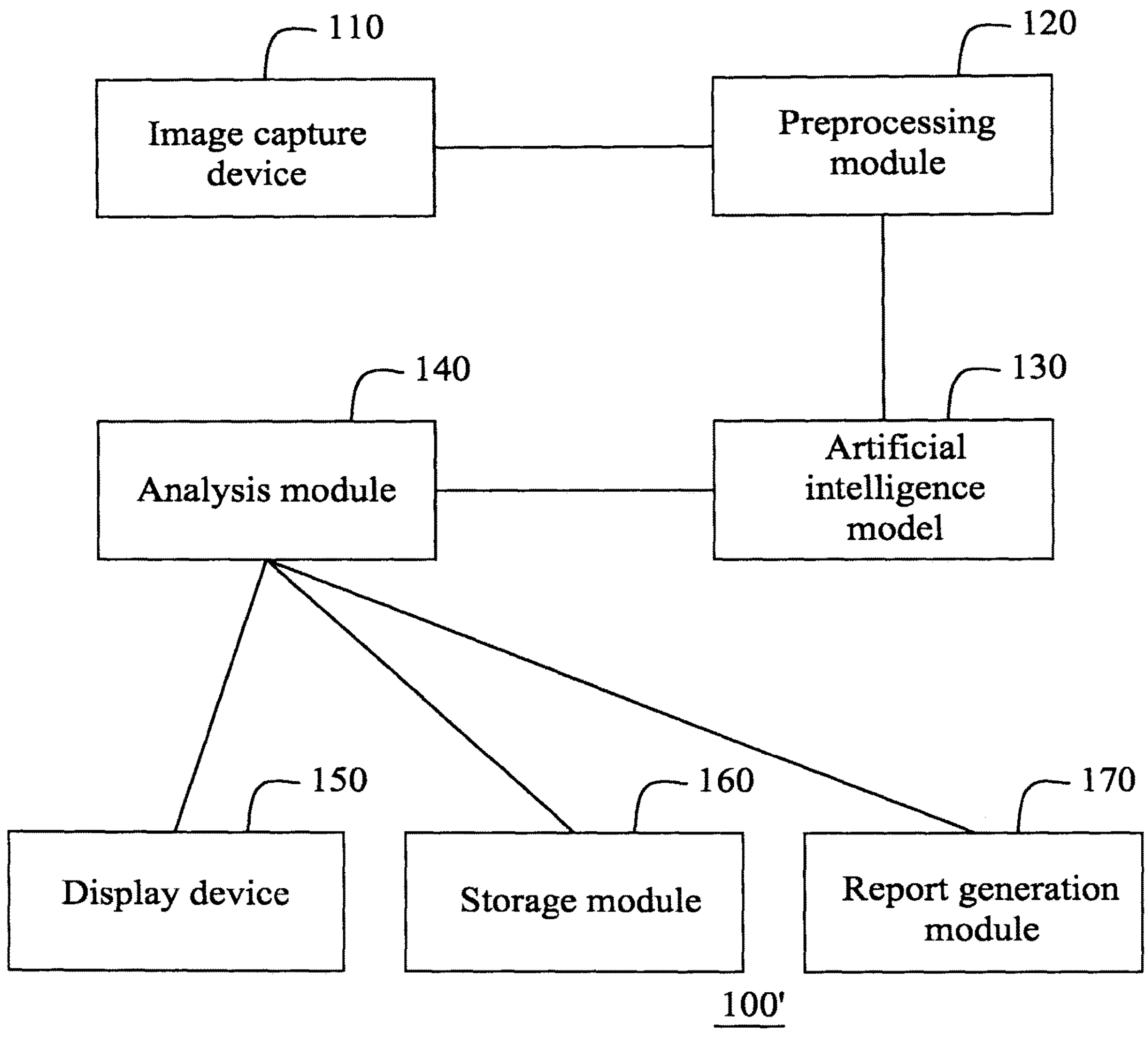
FIG. 1B illustrates a second embodiment of the hair feature analysis system of the present invention.

Next, please refer to FIG. 1B, which illustrates a second embodiment of the hair feature analysis system of the present invention. In addition to the aforementioned image capture device 110, preprocessing module 120, artificial intelligence model 130, and analysis module 140, the hair feature analysis system 100' of the second embodiment further includes other components, such as a display device 150 for presenting analysis images and calculated hair features to the user, a storage module 160 for storing the analysis images and calculated hair features in a database, and a report generation module 170 for generating a report based on the calculated hair features. In the second embodiment, the report generation module 170 generates a comprehensive report based on the calculated hair features. This report may contain various types of information, such as charts, statistical data summaries, and written explanations of the data, and the report can also be shared with others, printed, or saved in digital format for further analysis or record keeping.

Figure 2:
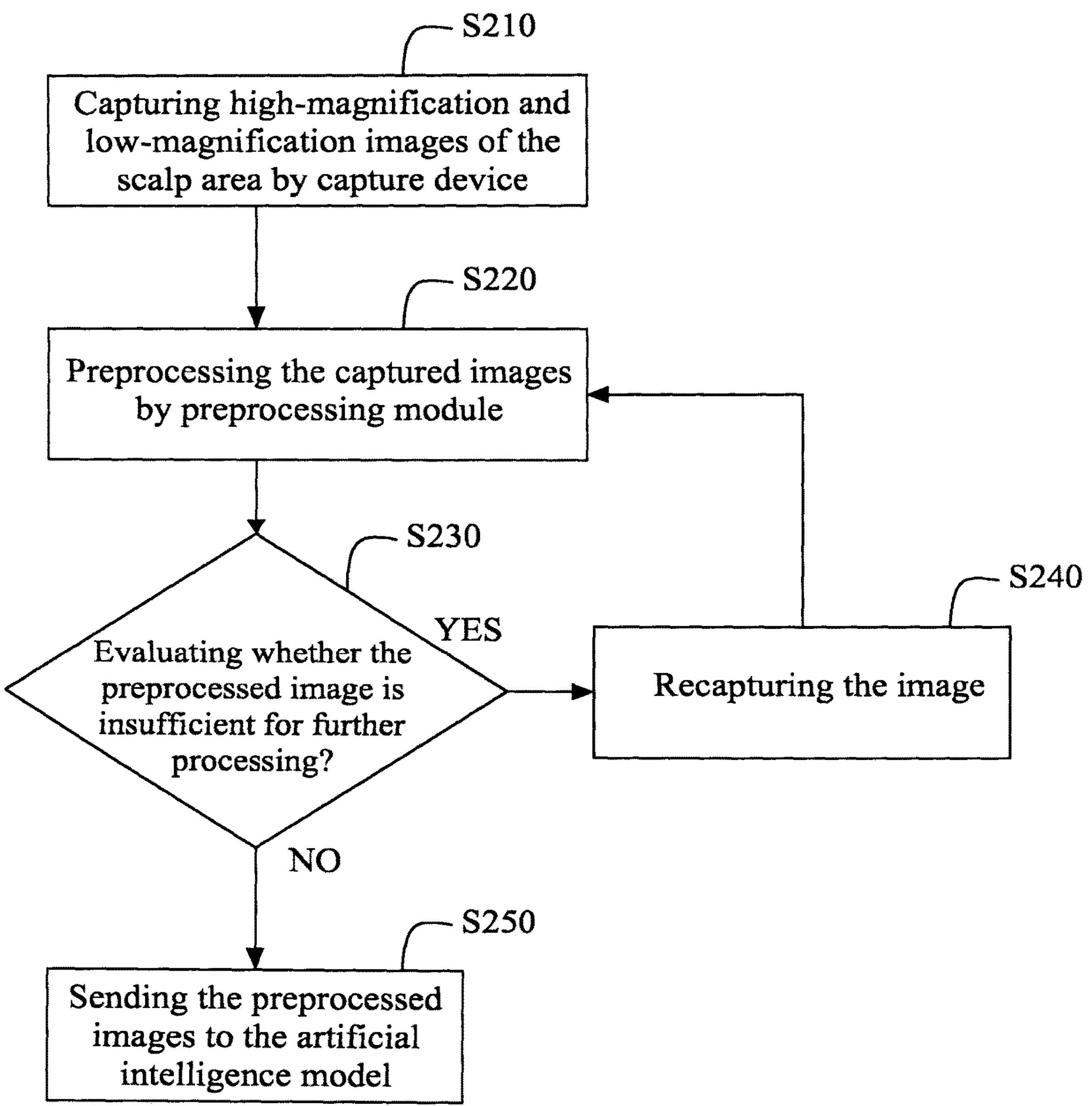
FIG. 2 is a flowchart illustrating the steps of capturing high magnification and low magnification images of a scalp area and preprocessing.

Please refer to FIG. 2, which illustrates a flowchart of the steps for capturing high-magnification and low-magnification images of the scalp area and preprocessing. In step S210, the capture device 110 captures high-magnification and low-magnification images of the scalp area. High-magnification images provide detailed information about follicles, while low-magnification images provide an overall view of hair density and distribution, which is beneficial for subsequent processing and analysis. In step S220, the preprocessing module 120 preprocesses the captured high-magnification and low-magnification images, such as noise reduction, resizing, and normalization, etc., to improve image quality and assist subsequent analysis. In step S230, the preprocessing module 120 evaluates the quality of the preprocessed images. If the image quality is insufficient for further processing, the system will enter step S240; otherwise, the process will proceed to step S250.

In step S240, the preprocessing module 120 will command the image capture device 110 to automatically recapture the image or notify the operator of the hair feature analysis system 100 to manually recapture the image. When a new image is captured, the process returns to step S220 for preprocessing. In step S250, the preprocessed high-magnification and low-magnification images are sent to the artificial intelligence model 130. Afterwards, the process continues with hair feature analysis, the details of which will be described in the following paragraphs.

Figure 3A:
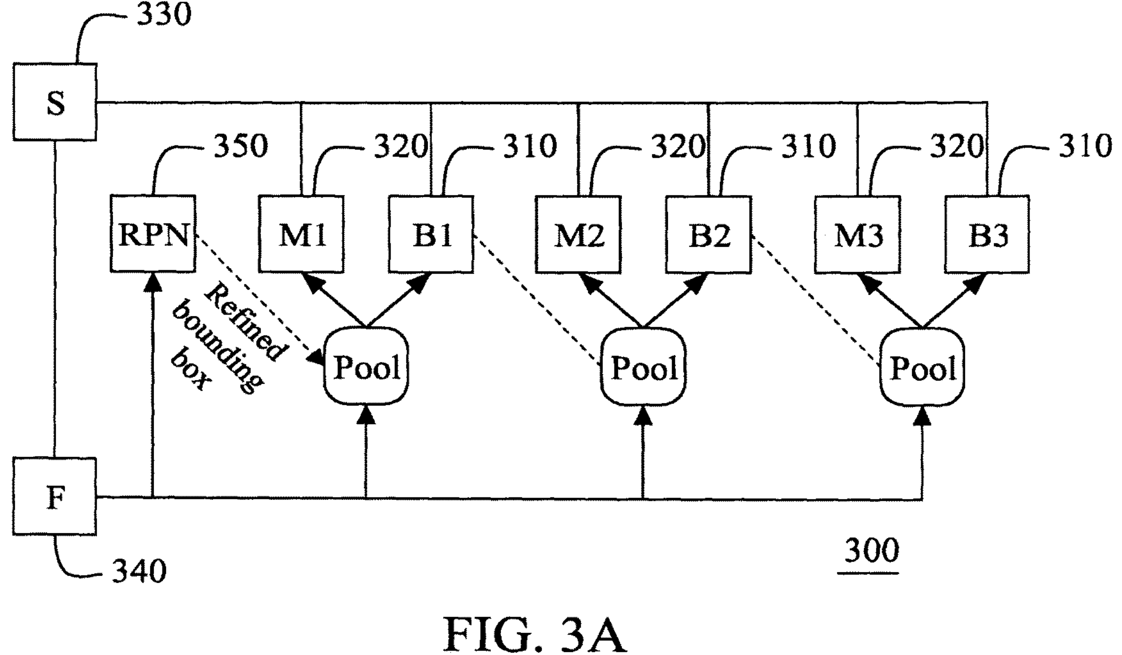
FIG. 3A illustrates a schematic diagram of a hybrid task cascade model.

Please refer to FIG. 3A, which illustrates a schematic diagram of a Hybrid Task Cascade model, hereinafter referred to as the HTC model. The HTC model 300 is a powerful deep learning model that performs excellently in object detection and segmentation tasks. The HTC model 300 includes multiple stages, each of which contains a bounding box detection framework branch 310 and an instance segmentation mask branch 320. The HTC model 300 also includes a semantic segmentation module 330 for processing the entire image, which is constructed using a fully convolutional model in this embodiment. The semantic segmentation module 330 is built based on the output of the Feature Pyramid Network 340. Then, the Region Proposal Network 350 generates a set of region proposals. To integrate multi-level features, the semantic segmentation model 330 combines mid-level features with higher-level features containing global information and lower-level features containing local information. In the HTC model 300, the bounding box branch 310 and mask branch 320 of each stage take the features extracted from the backbone network (i.e., the Region Proposal Network 350) as input, and also utilize the semantic features of the semantic segmentation module 330. This fusion of semantic features with features extracted by the ROI pooling operation or ROIAlign operation enhances the performance of the HTC model 300 in object detection and segmentation tasks.

In summary, the HTC model 300 uses the Feature Pyramid Network 340 to extract multi-scale features from the input image. Then, the Region Proposal Network 350 generates a set of region proposals. Each stage refines the region proposals, outputs the final bounding box coordinates of the detected objects, and predicts a binary mask for each detected object in the refined bounding box. The semantic segmentation branch 330 provides additional spatial context to improve object detection and segmentation in cluttered backgrounds. The output of the HTC model 300 includes multiple detected hair follicles and multiple hairs, which are subsequently used by the analysis module 140 to calculate various hair features, such as average hair diameter, fine hair density ratio, and total hair density ratio. For a more detailed description of the Hybrid Task Cascade model, please refer to the paper "Hybrid Task Cascade for Instance Segmentation" (arxiv.org/abs/1901.07518).

Figure 3B:
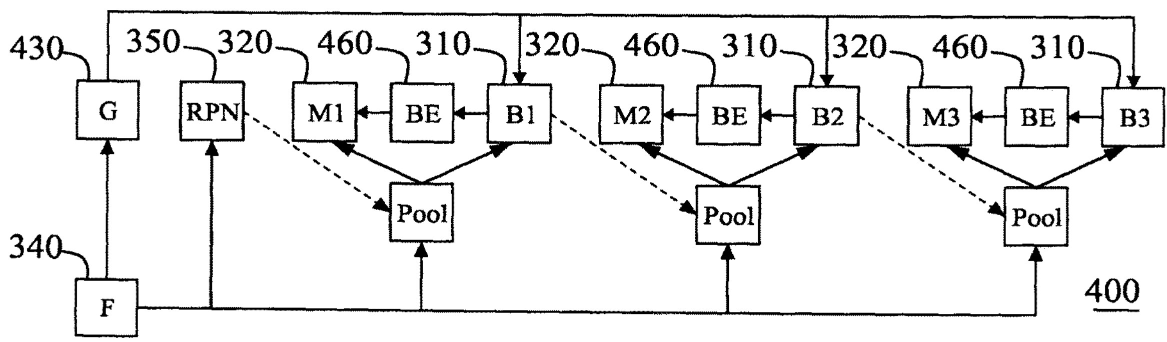
FIG. 3B illustrates a schematic diagram of the HTC enhanced model of the present invention.

Please refer to FIG. 3B, which illustrates a schematic diagram of the enhanced HTC model of the present invention. In this enhanced HTC model 400, the semantic segmentation module 330 in the original HTC model 300 (as shown in FIG. 3A) is replaced with a global feature enhancement module 430. In addition, the enhanced HTC model 400 also includes at least one box-mask enhancement module 460. This box-mask enhancement module creates a stronger connection, enhancing the relationship between the bounding box branch 310 and the mask branch 320, potentially improving the results of instance segmentation. Therefore, the enhanced HTC model 400 is more suitable for simultaneous detection of hair follicles and calculation of hair width required in the hair feature analysis system 100. That is, the enhanced HTC model 400 retains the advantages of the original HTC model 300, but introduces technical features added or modified for hair analysis. In other words, by replacing the semantic segmentation module 330 with the global feature enhancement module 430 and adding the box-mask enhancement module 460, the enhanced HTC model 400 can effectively handle the unique challenges associated with hair follicle detection and hair strand segmentation, ultimately leading to improved hair analysis results.

Figure 4A:
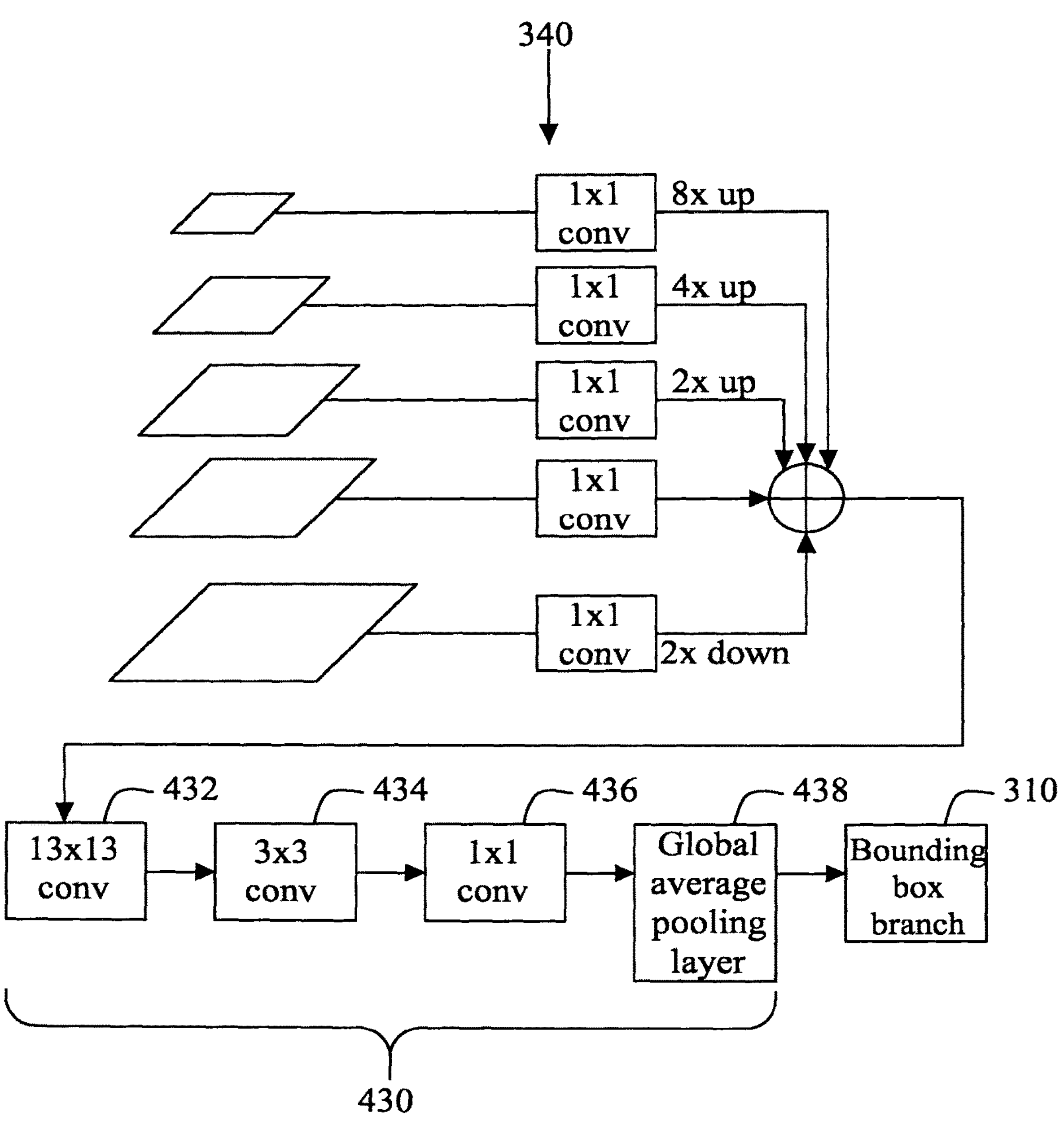
FIG. 4A illustrates a schematic diagram of a global feature enhancement module.

Please refer to FIG. 4A, which illustrates a schematic diagram of the global feature enhancement module. The global feature enhancement module 430 is designed to enhance the global features extracted from the Feature Pyramid Network 340 and integrate them into the enhanced HTC model 400, thereby improving the performance of the enhanced HTC model 400. In this embodiment, the output of the Feature Pyramid Network 340 is first connected to a 13×13 convolutional layer 432. This 13×13 convolutional layer 432 is responsible for capturing complex and detailed global features from the Feature Pyramid Network 340. The output of this 13×13 convolutional layer 432 is connected to a 3×3 convolutional layer 434, which is used to extract and refine local features from the input (i.e., the output of the 13×13 convolutional layer 432), enhancing the representation of global features. Subsequently, the output of the 3×3 convolutional layer 434 is connected to a 1×1 convolutional layer 436. This 1×1 convolutional layer 436 acts as a bottleneck, reducing the dimensionality of features and compressing information while retaining key features. The output of this 1×1 convolutional layer 436 is connected to a global average pooling layer 438. The global average pooling layer 438 calculates the average of the input feature map, generating a compact representation that captures global context information. Then it outputs the generated feature map, which is used to improve the performance of the enhanced HTC model 400 in detecting hair follicles and calculating hair width. By incorporating the global feature enhancement module 430 into the enhanced HTC model 400, the hair feature analysis system 100 can better analyze hair features and provide valuable insights about hair health and personalized hair care recommendations.

Figure 4B:
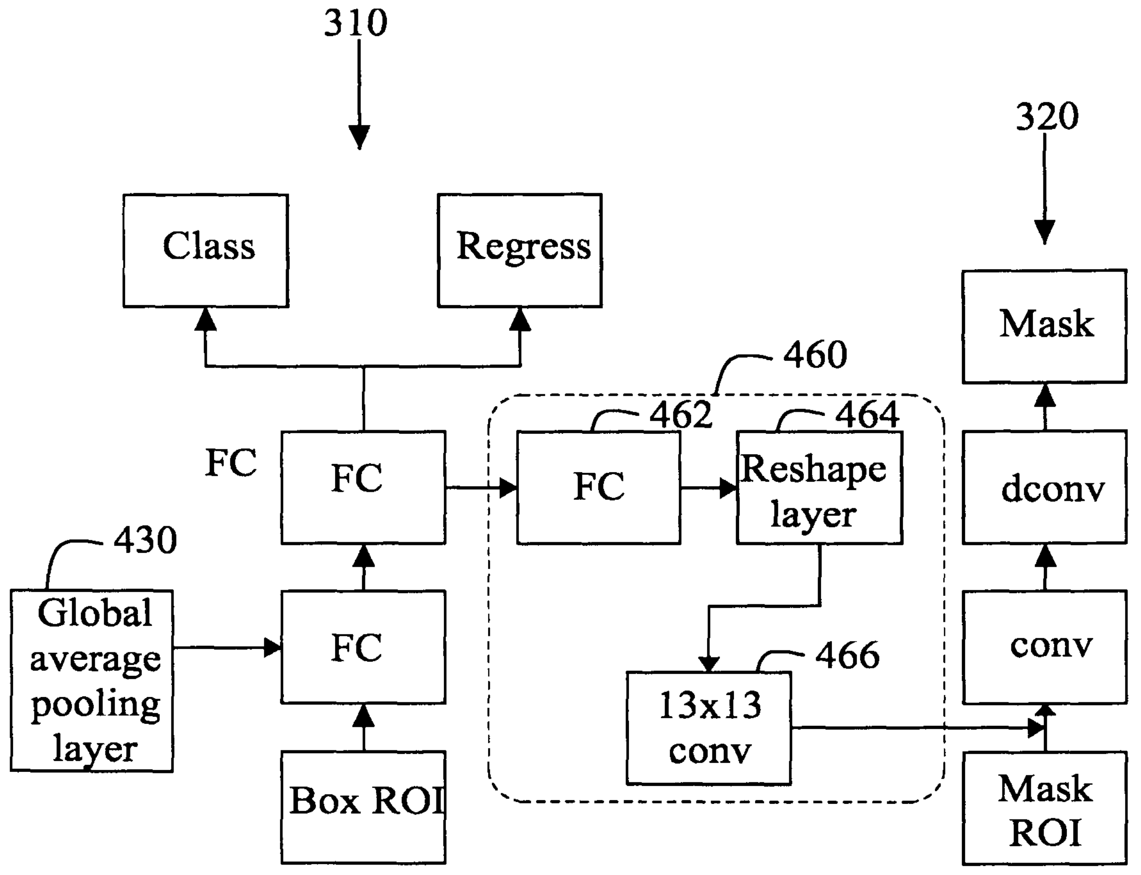
FIG. 4B illustrates a schematic diagram of a framework-mask enhancement module.

Please refer to FIG. 4B, which illustrates a schematic diagram of the box-mask enhancement module. The box-mask enhancement module 460 aims to create a stronger connection, combining the bounding box branch 310 and the mask branch 320, which may potentially improve the quality of instance segmentation results. In this embodiment, the box-mask enhancement module 460 includes a fully connected layer 462, a reshape layer 464, and a 13×13 convolutional layer 466. The fully connected layer 462 is connected to one of the output layers of the bounding box branch 310, with an output dimension of N×4096, for example, where N represents the number of detected bounding boxes. The function of the fully connected layer 462 is to capture features from the bounding box branch 310, which can improve the prediction effect of the mask branch 320.

Afterwards, the output tensor of the fully connected layer 462 is transformed from N×40*96 to N×256*14*14 by the reshape layer 464. This operation allows the tensor to match the size required by the following 13×13 convolution layer 466. The output of the reshape layer 464 is connected to the 13×13 convolution layer 466, which in turn connects to the mask branch 320. By connecting the features of the bounding box branch 310 to the mask branch 320 in this way, the box-mask enhancement module 460 can make the predictions of the mask branch 320 more accurate. Please note that in FIG. 4A and FIG. 4B, the convolution layer is abbreviated as "conv", the deconvolution layer is abbreviated as "dconv", and the fully connected layer is abbreviated as "FC".

Next, two embodiments of the configuration of the box-mask enhancement module will be introduced. In one embodiment, as shown in FIG. 3B, a box-mask enhancement module 460 is placed between the bounding box branch 310 and the mask branch 320 at each stage of the enhanced HTC model 400. This design helps to propagate more accurate bounding box information to the mask prediction process at each stage. By incorporating the box-mask enhancement module 460, the enhanced HTC model 400 can generate more accurate mask predictions and achieve better alignment between the bounding boxes and masks.

Figure 5:
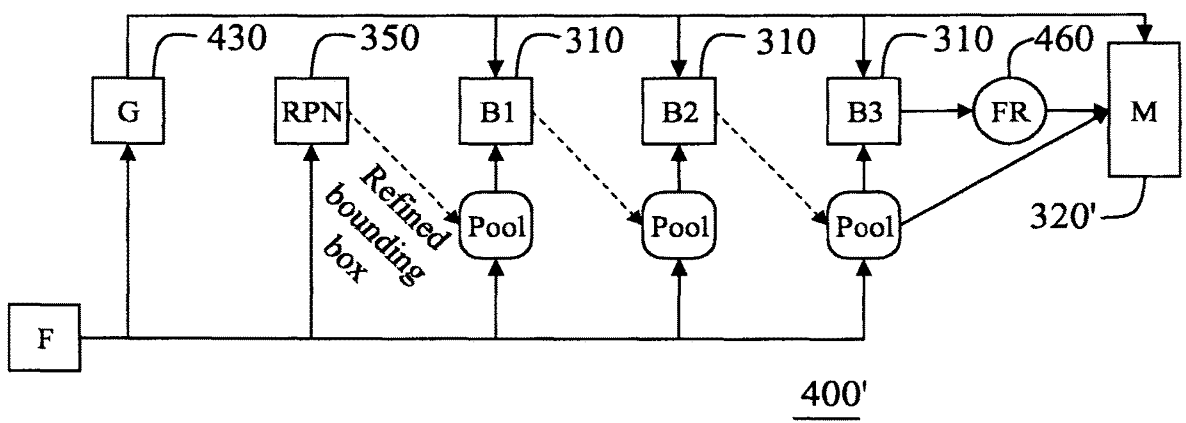
FIG. 5 illustrates a schematic diagram of another embodiment of the HTC enhanced model.

Then, please refer to FIG. 5, which illustrates a schematic diagram of another embodiment of the enhanced HTC model. The mask branch 320' is placed after the last bounding box branch 310, and the box-mask enhancement module 460 is used to connect them. The focus of this design is to improve mask prediction in the final stage of the enhanced HTC model 400', so that the most refined bounding box information can be used. By using the box-mask enhancement module 460 to connect the final bounding box branch 310 with the mask branch 320', the enhanced HTC model 400' may generate more accurate instance masks, which are better aligned with the detected bounding boxes.

Figure 6:
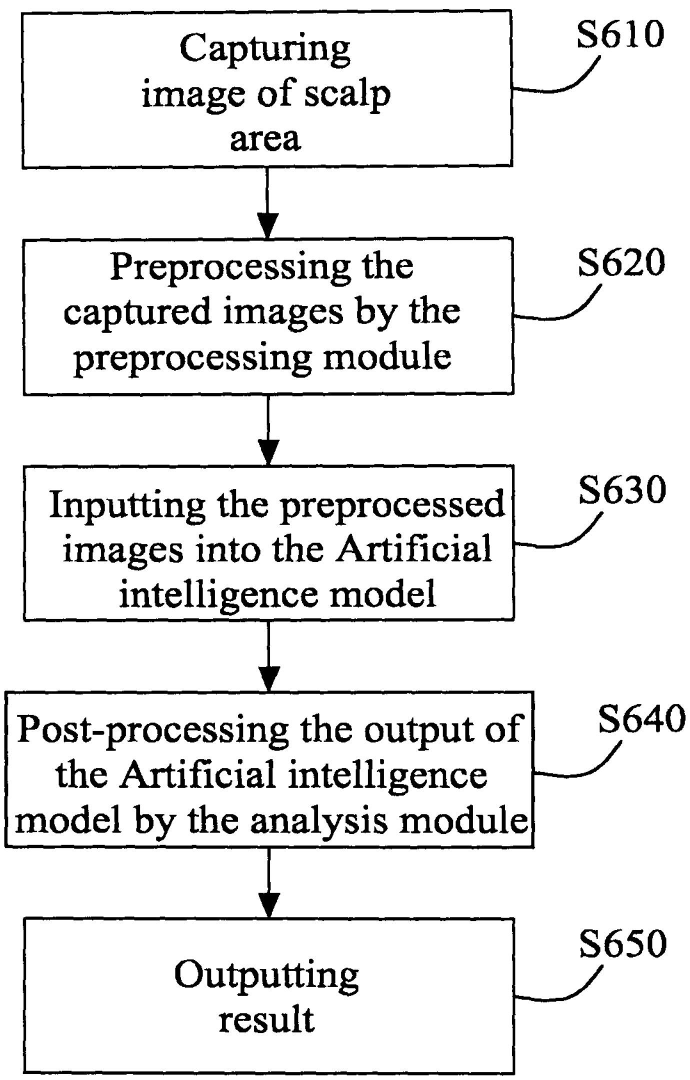
FIG. 6 illustrates a flowchart of the hair feature analysis method of the present invention.

Next, a comprehensive description of the hair feature analysis method of this invention will be given. Please refer to FIG. 6, which illustrates a flowchart of the hair feature analysis method of this invention. The hair feature analysis method in this invention includes several steps. First, in step S610, a high magnification image and a low magnification image of a scalp area are captured. Then, in step S620, the captured images are preprocessed by the preprocessing module 120, including various techniques such as resizing, normalization, and augmentation, to prepare the input images for use by the Artificial intelligence model 130.

Next, in step S630, the preprocessed images are input into the Artificial intelligence model 130, which uses the enhanced HTC model 400 to simultaneously perform hair follicle detection and calculate hair width. Then, in step S640, the output of the Artificial intelligence model 130 is post-processed by the analysis module 140. Afterward, in step S650, the results of the analysis module 140 are output.

Here, we will provide a more detailed introduction to steps S640 and S650, starting with step S640. After the Artificial intelligence model 130 simultaneously detects multiple hair follicles in the scalp area and calculates the width of multiple hairs from the preprocessed images, the analysis module 140 receives the information output by the Artificial intelligence model 130. Based on this information, the analysis module 140 segments the hair, with the middle segment of each hair being selected as the basis for width calculation. Then, by analyzing the selected hair segments, the number of pixels corresponding to the hair width is determined. Subsequently, the analysis module 140 converts the pixel count representing hair width into a real-world measurement scale (such as micrometers) to provide accurate hair width. In addition, the analysis module 140 also calculates the fine hair density ratio, which is the ratio of fine hair (i.e., hair with a diameter smaller than a certain threshold) to the total number of hairs. This indicator can help evaluate hair strength and identify potential hair thinning or breakage problems. Furthermore, the analysis module 140 also calculates the total hair density ratio, which is the ratio of the total number of hair follicles in the examined scalp area to the area. This parameter helps identify the degree of hair loss or thinning.

Once the analysis module 140 calculates these hair features, the hair feature analysis system 100 proceeds to step S650, presenting the results to the user. In step S650, the display device 150 displays the analyzed images and calculated hair features, providing the user with a visualized result of the hair analysis (as shown in FIG. 8). In addition, the storage module 160 stores the analyzed images and calculated hair features in a database for easy retrieval and comparison of results. This feature can be used to track hair health progress or evaluate the effectiveness of hair care treatments. Furthermore, the report generation module 170 generates a report based on the calculated hair features. This report may include a summary of the hair analysis results, personalized hair care recommendations, and any other information related to the user's hair health. The report can be printed, emailed, or shared with the user in other ways for reference and discussion.

Figure 7A:
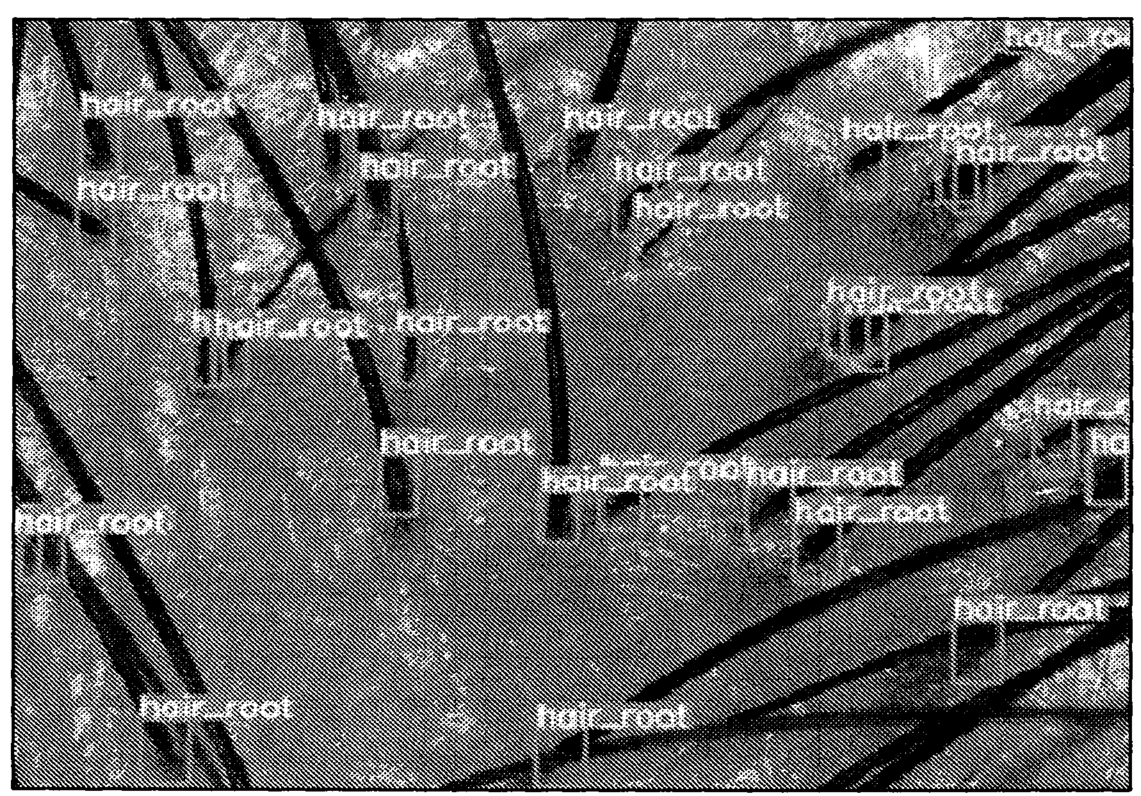
FIGS. 7A to 7C show real-world images output by the hair feature analysis system in actual operation.
Figure 7B:
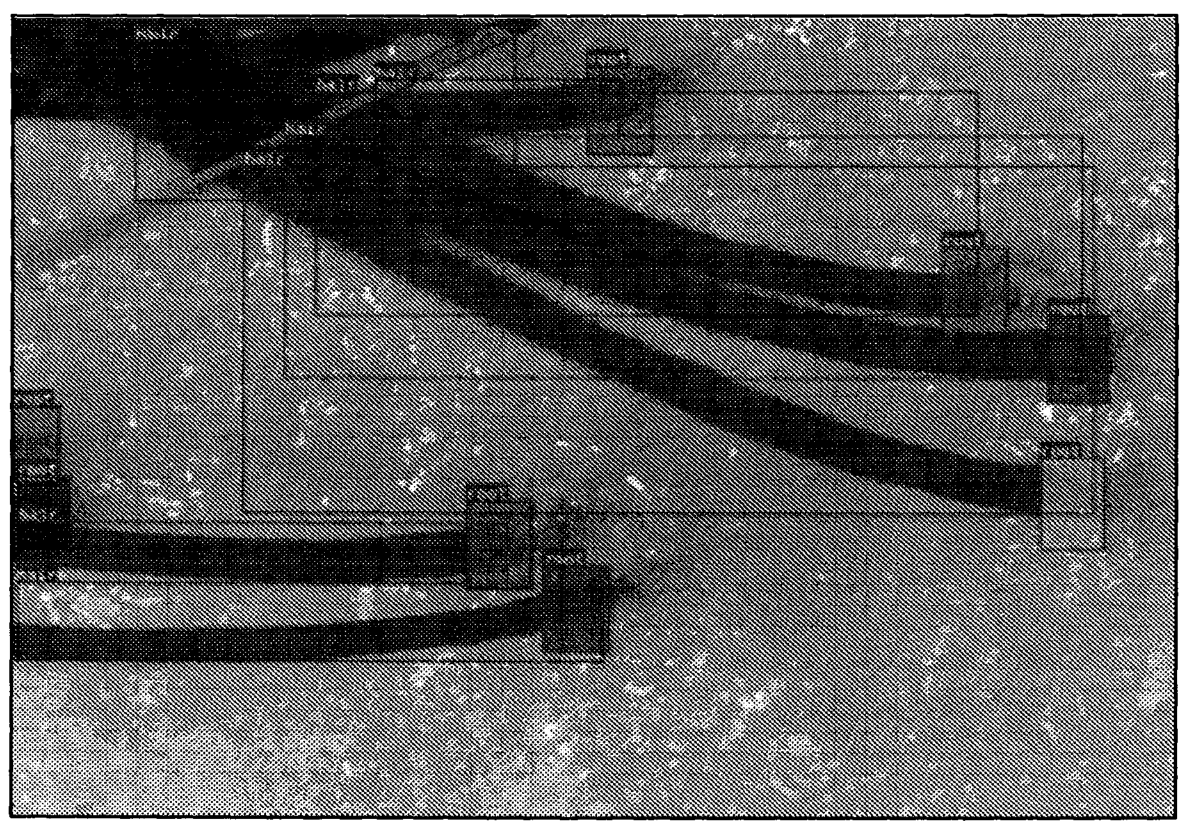
Figure 7C:
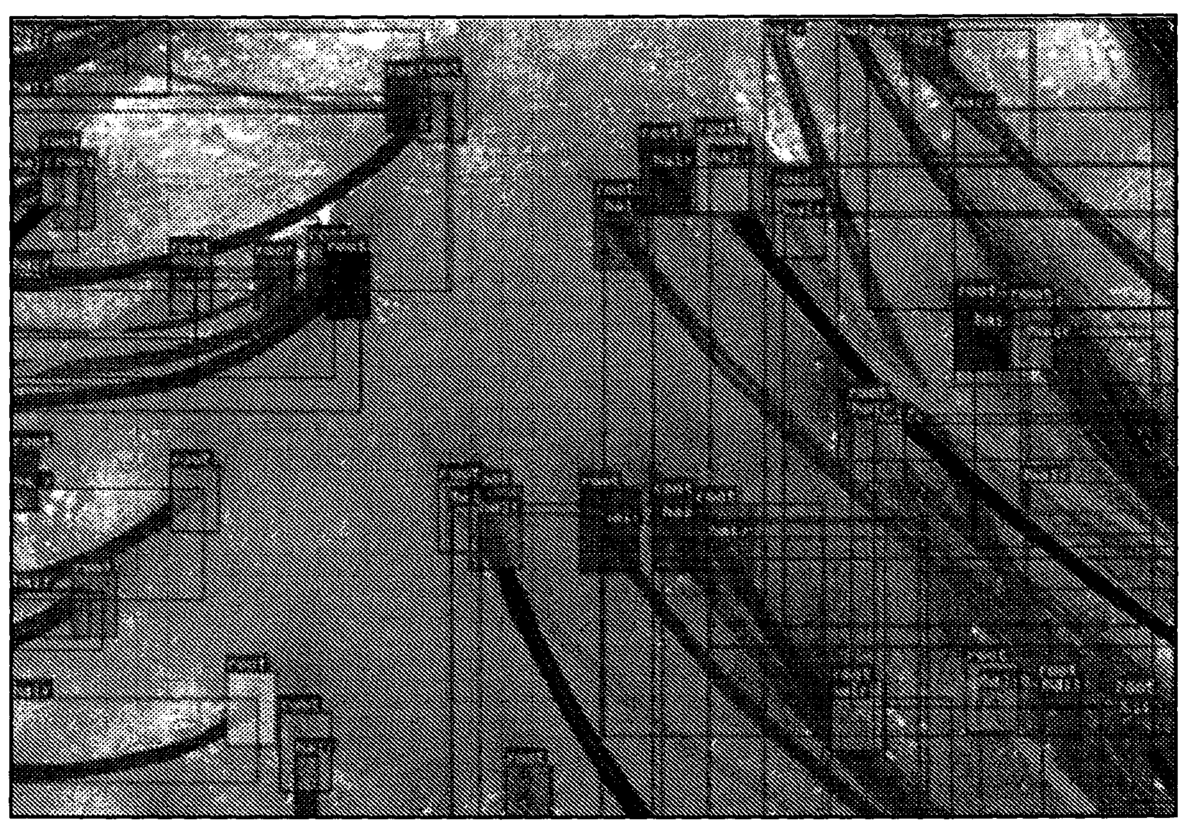

Please refer to FIGS. 7A to 7C, which show real-life images output by the hair feature analysis system in actual operation. These real-life images demonstrate the ability of the Artificial intelligence model 130 of this invention to accurately identify hair follicles and hair, serving as empirical evidence of the effectiveness of the Artificial intelligence model 130 in detecting and analyzing hair-related features. It should be noted that the real-life images in FIGS. 7A to 7C are the output results of the Artificial intelligence model 130 including the enhanced HTC model 400. In FIG. 7A, the Artificial intelligence model 130 is able to effectively distinguish individual hair follicles from the surrounding skin and hair strands, highlighting its accuracy in detecting the location of hair follicles. This ability to accurately detect hair follicles enables the hair feature analysis system 100 to provide reliable measurements of hair density and distribution.

FIG. 7B demonstrates the ability of the Artificial intelligence model 130 to identify individual hairs. With effective identification of individual hairs, the width of each hair can be accurately calculated, thus providing valuable information about hair health to the user, such as average hair diameter, fine hair density ratio, and total hair density ratio. FIG. 7C shows that the Artificial intelligence model 130 successfully segmented individual hairs and hair follicles, also confirming the effectiveness of the enhanced HTC model 400 in object detection and instance segmentation tasks. This segmentation allows the hair feature analysis system 100 to simultaneously detect hair follicles and calculate hair width, thereby improving the analysis results. The real-life images shown in FIGS. 7A to 7C provide a powerful visual proof of the ability of the Artificial intelligence model 130 to accurately detect and analyze hair follicles and hair, while also demonstrating the practicality and effectiveness of the hair feature analysis system 100 of this invention in a real-world environment.

In the above embodiments, the Artificial intelligence model 130 uses the HTC model and the enhanced HTC model as examples, but the Artificial intelligence model 130 can also use the R-CNN model. When the Artificial intelligence model 130 is an R-CNN model, the first step is to generate potential bounding boxes or region proposals for the follicles in the input image. Selective search algorithms or other region proposal algorithms can be used, and regions of interest are determined based on color, texture, and size. Then, for each region of interest, the R-CNN model applies a pre-trained convolutional neural network (CNN) to extract meaningful features. The CNN helps identify patterns and features of follicles and hair, enabling the model to accurately identify and segment them. After feature extraction, a classifier is applied to each region of interest to determine whether it contains a follicle. The classifier, for example, could be a support vector machine, which uses the features extracted in the previous step to make decisions. Next, bounding box regression is performed in parallel with the classification step, optimizing the coordinates of the proposed bounding boxes to better frame the follicles, thereby improving the accuracy of follicle detection and segmentation. Afterward, the R-CNN model can pass the output data to the analysis model 140 for subsequent processing.

In addition, the Artificial intelligence model 130 can also use variants of other R-CNN models, such as the Cascade R-CNN model or the Mask R-CNN model. The Cascade R-CNN model can refer to the paper "Cascade R-CNN: High Quality Object Detection and Instance Segmentation" (arxiv.org/abs/1906.09756), and the Mask R-CNN model can refer to the paper "Mask R-CNN" (arxiv.org/abs/1703.06870)

Although the invention has been disclosed and illustrated with reference to particular embodiments, the principles involved are susceptible for use in numerous other embodiments that will be apparent to persons skilled in the art. This invention is, therefore, to be limited only as indicated by the scope of the appended claims

What is claimed is:

1. A hair feature analysis method, comprising:

capturing a high magnification image and a low magnification image of a scalp area, providing detailed information about follicles by the high magnification image, providing an overall view of hair density and distribution by the low magnification image;

preprocessing the high magnification image and low magnification image, wherein the step of preprocessing the captured high magnification image and low magnification image includes denoising, resizing, normalizing, or recapturing the image;

inputting the preprocessed high magnification image and low magnification image into an artificial intelligence model, simultaneously detecting multiple hair follicles and multiple hair widths in the scalp area;

calculating at least one hair feature from the high magnification image and the low magnification image analyzed by the artificial intelligence model, wherein the hair feature includes average hair diameter, thin hair density ratio, or total hair density ratio; and wherein, the artificial intelligence model is a Region-based Convolutional Neural Network (R-CNN) variant in the form of an HTC enhanced model that is modified from a hybrid task cascade model, and the HTC enhanced model is formed by:

replacing a semantic segmentation module in the hybrid task cascade model with a global feature enhancement module;

connecting refined semantic features from the global feature enhancement module with multiple framework branches; and introducing at least one framework-mask enhancement module, connecting the framework branches and at least one mask branch.

2. The hair feature analysis method according to claim 1, wherein the global feature enhancement module includes multiple convolutional layers with different kernel sizes to extract multi-scale features.

3. The hair feature analysis method according to claim 1, wherein the HTC enhanced model has a framework branch and a mask branch at each stage, and the number of the framework-mask enhancement modules is multiple, each framework-mask enhancement module is connected between the framework branch and the mask branch at each stage.

4. The hair feature analysis method according to claim 1, wherein the HTC enhanced model has a framework branch at each stage and one mask branch, and the framework-mask enhancement module is configured between the last framework branch and the mask branch, serving to connect the last framework branch and the mask branch.

5. The hair feature analysis method according to claim 1, further comprising:

displaying the analyzed image and calculated hair features to a user;

storing the analyzed image and calculated hair features in a database; or generating a report based on the calculated hair features.

6. A hair feature analysis system, comprising:

an image capturing device for capturing a high magnification image and a low magnification image of a scalp area, wherein the high magnification image provides detailed information about follicles, and the low magnification image provides an overall view of hair density and distribution;

a preprocessing module for preprocessing the captured high magnification image and low magnification image, wherein the step of preprocessing the captured high magnification image and low magnification image includes denoising, resizing, normalizing, or recapturing the image;

an artificial intelligence model for simultaneously detecting multiple hair follicles and calculating multiple hair widths in the high magnification image and low magnification image, wherein the artificial intelligence model is a variant of a Region-based Convolutional Neural Network (R-CNN) model; and an analysis module for receiving the high magnification image and low magnification image analyzed by the artificial intelligence model and calculating at least one hair feature, wherein the hair feature includes average hair diameter, thin hair density ratio, or total hair density ratio;

wherein the artificial intelligence model is an HTC enhanced model, which is modified from a hybrid task cascade model, and the HTC enhanced model is formed by:

replacing a semantic segmentation module in the hybrid task cascade model with a global feature enhancement module;

connecting refined semantic features from the global feature enhancement module with multiple framework branches; and introducing at least one framework-mask enhancement module, connecting the framework branches and at least one mask branch.

7. The hair feature analysis system according to claim 6, wherein the global feature enhancement module includes multiple convolutional layers with different kernel sizes to extract multi-scale features.

8. The hair feature analysis system according to claim 6, wherein the HTC enhanced model has a framework branch and a mask branch at each stage, and the number of the framework-mask enhancement modules is multiple, each framework-mask enhancement module is connected between the framework branch and the mask branch at each stage.

9. The hair feature analysis system according to claim 6, wherein the HTC enhanced model has a framework branch at each stage and one mask branch, the framework-mask enhancement module is configured between the last framework branch and the mask branch, and the framework-mask enhancement module connects the last framework branch and the mask branch.

10. The hair feature analysis system according to claim 6, further comprising:

a display device for displaying the analyzed image and calculated hair features to a user;

a storage module for storing the analyzed image and calculated hair features in a database; or a report generation module for generating a report based on the calculated hair features.

* * * * *